United States Patent
LeBrun (10) Patent No.: US 10,445,472 B2
(45) Date of Patent: Oct. 15, 2019

(54) SYSTEM AND METHOD FOR MONITORING PILL CONTAINER ACTIVITY

(71) Applicant: PILLSY, INC., Seattle, WA (US)

(72) Inventor: Jeffrey R. LeBrun, Seattle, WA (US)

(73) Assignee: Pillsy, Inc., Seattle, WA (US)

( * ) Notice: Subject to any disclaimer, the term of this patent is extended or adjusted under 35 U.S.C. 154(b) by 742 days.

(21) Appl. No.: 14/824,231

(22) Filed: Aug. 12, 2015

(65) Prior Publication Data

US 2016/0048657 A1    Feb. 18, 2016

Related U.S. Application Data (60) Provisional application No. 62/036,272, filed on Aug. 12, 2014.

(51) Int. Cl.
| | |
|---|---|
| *G06F 19/00* | (2018.01) |
| *B65D 51/24* | (2006.01) |
| *B65D 50/04* | (2006.01) |
| *A61J 1/14* | (2006.01) |

(52) U.S. Cl.
CPC ........ *G06F 19/3462* (2013.01); *A61J 1/1412* (2013.01); *B65D 50/043* (2013.01); *B65D 51/24* (2013.01); *B65D 51/248* (2013.01); *G06F 19/3418* (2013.01); *A61J 2200/30* (2013.01); *A61J 2200/74* (2013.01)

(58) Field of Classification Search
CPC .............. G06F 19/3462; G06F 19/3456; A61J 1/1412; A61J 7/0472; A61J 7/0436; B65D 51/248; B65D 2101/0015; B65D 83/0409
USPC .......................................................... 705/2
See application file for complete search history.

(56) References Cited

U.S. PATENT DOCUMENTS

| | | | |
|---|---|---|---|
| 5,751,661 A | * | 5/1998 | Walters ................. A61J 7/0409 221/2 |
| 6,518,523 B1 | | 2/2003 | Chou |
| 7,081,807 B2 | | 7/2006 | Lai |
| 7,446,272 B2 | | 11/2008 | Chou |
| 7,928,835 B1 | | 4/2011 | Jovanov et al. |
| 8,092,224 B2 | | 1/2012 | Walker et al. |
| 8,116,907 B2 | | 2/2012 | Hyde et al. |

(Continued)

FOREIGN PATENT DOCUMENTS

| | | |
|---|---|---|
| WO | 2010078558 A1 | 7/2010 |
| WO | 2013120029 A1 | 8/2013 |

(Continued)

OTHER PUBLICATIONS

PCT/US2018/040150 search report published WO2019/006212 dated Mar. 1, 2019.

*Primary Examiner* — Hiep V Nguyen
(74) *Attorney, Agent, or Firm* — Carrie M. Stroup (57) ABSTRACT

A cap for a medication container includes a housing with a top portion and a bottom portion. The top and bottom portions together define a cavity therebetween. A sliding plate is disposed in the cavity adjacent the bottom portion. A microcontroller with a contact sensor is disposed in the cavity between the top portion and the sliding plate. The sliding plate is configured to slide toward and activate the contact sensor where the cap is secured to the medication container in a closed state. The sliding plate is also configured to slide away from and not activate the contact sensor where the cap is removed from the medication container in an open state.

21 Claims, 12 Drawing Sheets

(56) References Cited

U.S. PATENT DOCUMENTS

| | | |
|---|---|---|
| 8,362,914 B2 | 1/2013 | Hyde et al. |
| 8,666,926 B1 | 3/2014 | Nease et al. |
| 8,754,769 B2 | 6/2014 | Stein et al. |
| 2001/0028308 A1* | 10/2001 | De La Huerga .. A61M 5/14212 340/573.1 |
| 2002/0126585 A1* | 9/2002 | Osberg ................ A61J 7/0472 368/107 |
| 2003/0063522 A1 | 4/2003 | Sagar |
| 2003/0069540 A1 | 4/2003 | Fowler et al. |
| 2005/0047114 A1 | 3/2005 | Harrell et al. |
| 2007/0171627 A1 | 7/2007 | Hsu |
| 2007/0201220 A1 | 8/2007 | Ulicny |
| 2009/0134181 A1 | 5/2009 | Wachman et al. |
| 2010/0001812 A1 | 1/2010 | Kausch |
| 2010/0270257 A1 | 10/2010 | Wachman et al. |
| 2012/0029693 A1 | 2/2012 | Bear et al. |
| 2014/0052468 A1 | 2/2014 | Burrows et al. |
| 2014/0108031 A1 | 4/2014 | Ferrara |
| 2014/0240094 A1 | 8/2014 | Stein et al. |
| 2014/0300273 A1 | 10/2014 | LeBrun et al. |

FOREIGN PATENT DOCUMENTS

| | | |
|---|---|---|
| WO | 2013127564 A1 | 9/2013 |
| WO | 2013158352 A1 | 10/2013 |
| WO | WO2019006212 A1 | 1/2019 |

\* cited by examiner

SYSTEM AND METHOD FOR MONITORING PILL CONTAINER ACTIVITY

CROSS-REFERENCE TO RELATED APPLICATIONS

This application claims the benefit of U.S. Provisional Application No. 62/036,272, filed on Aug. 12, 2014. The entire disclosure of the above application is hereby incorporated herein by reference.

FIELD

The present disclosure relates to systems and methods for increasing patient adherence to medication and nutrition regimens and, more particularly, to a smart pill cap for use with standard prescription medicine containers.

BACKGROUND

The statements in this section merely provide background information related to the present disclosure and may not constitute prior art.

Many people take medications, vitamins, and nutritional supplements on a regular basis as a way of life. However, a common problem is that people forget to take their medications or other pills on a regular basis, or as they are prescribed. Experts have estimated average medication adherence rates of 50% to 60%. According to the National Community Pharmacists Association, this costs about 125,000 lives and $290 billion in the United States alone. While there are several factors behind non-adherence, several studies have indicated that forgetfulness is a driving factor.

In light of these facts, there is a continuing need for a cost effective system and method of promoting patient adherence to medication and nutrition regimens. Desirably, increasing rates of patient adherence will improve patient outcomes, saving patient lives and reducing preventative costs borne by the healthcare system and society.

SUMMARY

In concordance with the instant disclosure, a cost effective system and method of promoting patient adherence to medication and nutrition regimens, which improves patient outcomes, saves patient lives, and reduces preventative costs borne by the healthcare system and society, is surprisingly discovered.

The present disclosure provides a device and method to assist people with managing either a) their medications or b) the medications of somebody whom they are caring for. In one embodiment of the disclosure, these medications are placed into a standard prescription pill container that is labeled and filled by a pharmacist. The standard prescription pill vial has a smart pill cap. Information about the medication, including the medication schedule, are programmed into a software application that connects to the smart pill cap attached to the pill container. The smart pill cap detects interactions with the pill container, including when it is opened and closed, and sends this information wirelessly to a remote computer. The remote computer can remind the user to take their medications when they forget. The remote computer can also send the user's medication adherence data to a remote server, where it may be shared with family members or their healthcare providers. The system can remind patients when to take their medications, provide information about the medications, monitor adherence to the prescribed medications, and can transmit this information to authorized individuals who can further assist patients in managing their conditions.

In one embodiment, a cap for a medication container includes a housing with a top portion and a bottom portion. The top portion and the bottom portion together define a cavity therebetween. A sliding plate is disposed in the cavity adjacent the bottom portion. A microcontroller with a switch type contact sensor is disposed in the cavity between the top portion and the sliding plate. The sliding plate is configured to slide toward and activate the contact sensor where the cap is secured to the medication container in a closed state. The sliding plate is configured to slide away from and not activate the contact sensor where the cap is removed from the medication container in an open state.

In another embodiment, a system for promoting adherence to a regimen by a patient includes the cap, and a first remote computer having a memory and a display. The first remote computer is in electronic communication with the cap. The first remote computer is configured to show on the display information corresponding with the sliding plate pressing against and activating the contact sensor. The information is indicative of an opening and a closing of the medication container over time.

In a further embodiment, a method for promoting adherence to a regimen by a patient, includes the steps of providing the system with the cap and the first remote computer, and maintaining the cap in a standby mode until the cap senses a change in state from one of the open state and the closed state. The cap is then caused to enter an active mode for a predefined period of time. The cap is configured to record the information from the contact sensor while in the active mode. The microcontroller of the cap then creates a sensor data log of the information, and communicates the sensor data log to the first remote computer.

Further areas of applicability will become apparent from the description provided herein. It should be understood that the description and specific examples are intended for purposes of illustration only and are not intended to limit the scope of the present disclosure.

DRAWINGS

The above, as well as other advantages of the present disclosure will become readily apparent to those skilled in the art from the following detailed description when considered in light of the accompanying drawings, in which.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
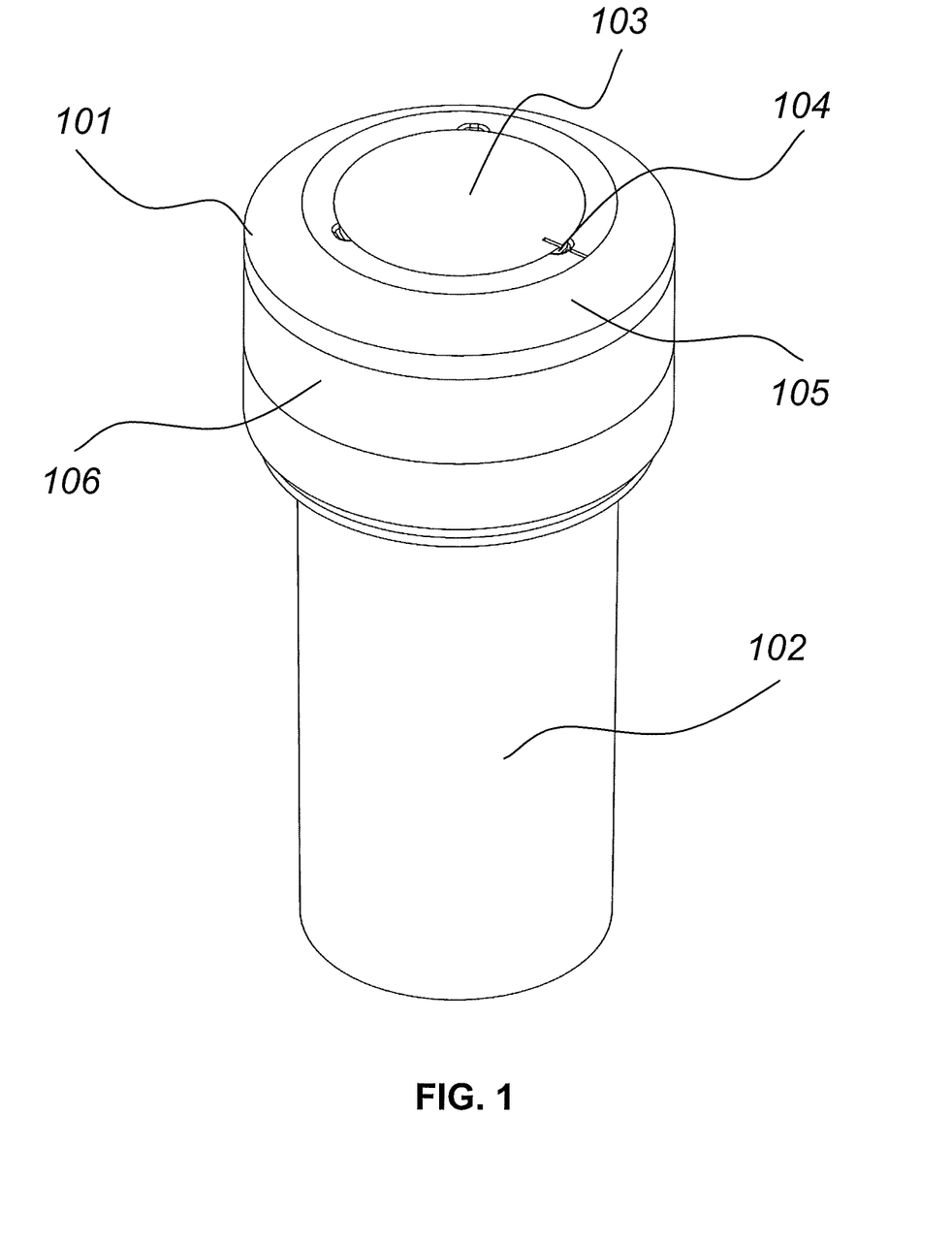
FIG. 1 is a perspective view of an assembly including a smart pill cap attached to a prescription pill container, according to one embodiment of the disclosure.

FIG. 1 illustrates a smart pill cap 101 that is capable of being removably coupled to a pill container 102, such as a vial. The smart pill cap 101 contains an internal switch-type contact sensor for detecting whether or not it is coupled to the container 102, thereby detecting whether the container is opened or closed. This information is stored in local memory that is also internal to the cap. As used herein, the term "memory" may include a non-transitory and tangible computer-readable storage medium, on which databases and processor-executable software code may be embodied. The smart pill cap 101 transmits the information to an external computer or gateway via a wireless radio connection. Audio reminders may be emitted from a speaker internal to the smart pill cap 101, which are configured to occur when the user does not open the container on a pre-scheduled basis.

In a particular embodiment, a top plate 103 is incorporated into the smart pill cap 101 that can be removed in order to expose a coin cell style battery. A gap 104 between the top plate 103 and the primary container body 105 permits the top plate 103 to be removed via a prying action, as well as permits sound emitted by the internal speaker to be heard by the user.

A silicone band 106 provides an improved grip on the smart pill cap while concealing a seam between the top and bottom portions of the smart pill cap assembly. The silicone band 106 may also be colored in a way that the user associates it with the display of one of their medications in the accompanying software of the smart pill cap 101.

The smart pill cap 101 can be placed on a prescription or over-the-counter pill container in order to track medication usage and adherence. The container 102 may be filled by a pharmacist, drug manufacturer, drug distributor, or wholesale provider.

Figure 2:
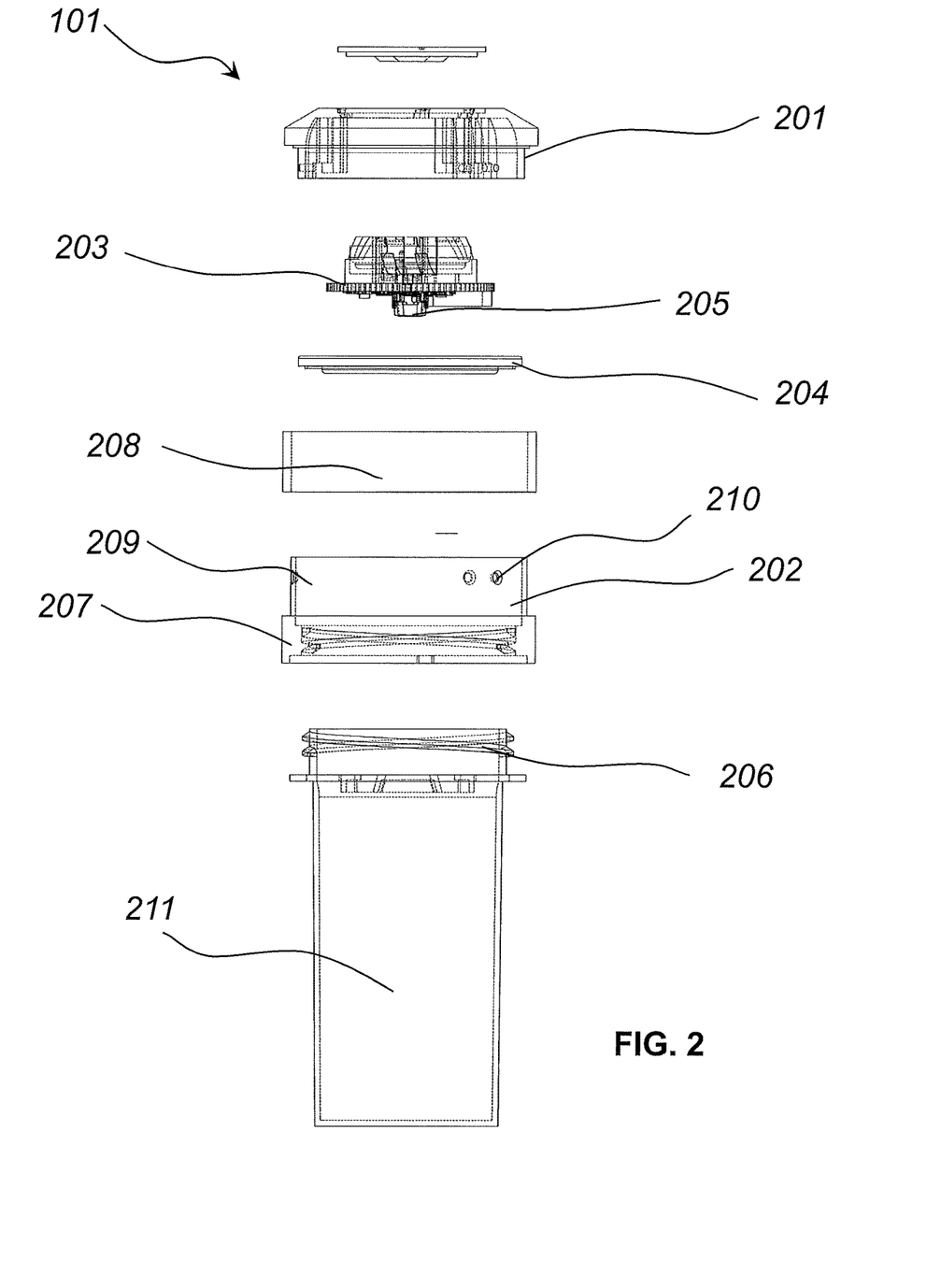
FIG. 2 is an exploded side elevational view of the assembly of FIG. 1.

FIG. 2 illustrates a sub-assembly of the smart pill cap 101 and integration with the pill container 102, according to one embodiment of the disclosure. A top portion 201 of the smart pill cap housing is securely attached to a bottom portion 202 of the smart pill cap housing, encasing a printed circuit board 203. Although the top portion 201 and the bottom portion 202 are described further herein as being distinct top and bottom pieces, separately formed and subsequently attached to one another, it should be appreciated that the top portion 201 and the bottom portion 202 may also be formed integrally as a single or unitary one-piece body, as desired.

The printed circuit board contains a switch type sensor 204, a wireless radio, memory, a speaker, and other electronic components. A sliding plate 204 is also encased by the top piece 201 of the housing and the bottom piece 202 of the housing. The sliding plate 204 presses down the switch type sensor 205 when the pill container 211 is attached to the smart pill cap 101 by tightening the threads 206 on the container with the threads 207 internal to the smart pill cap.

A silicone band 208 may be placed on the outside of the assembled smart pill cap 101. The silicone band 208 may fit into a groove 209 that permits a flush fitting within the side of the smart pill cap 101. The silicone band 208 may cover up screw holes 210 that are used to attach the top piece 201 and the bottom piece 202 of the smart pill cap 101.

Figure 3A:
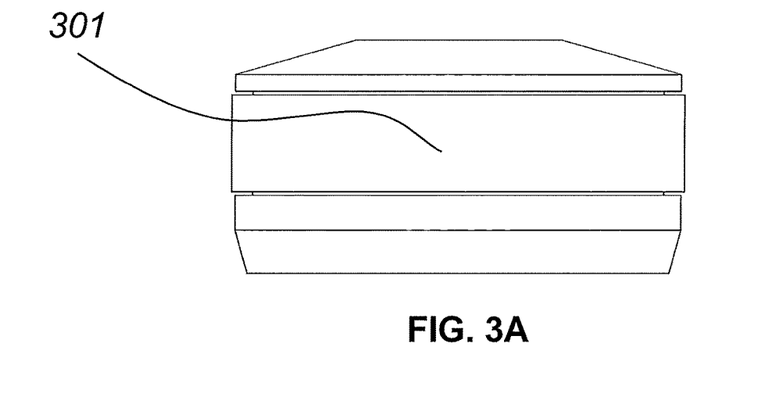
FIG. 3A is an enlarged side elevational view of the threaded smart pill cap of FIG. 1, shown without the prescription pill container.
Figure 3B:
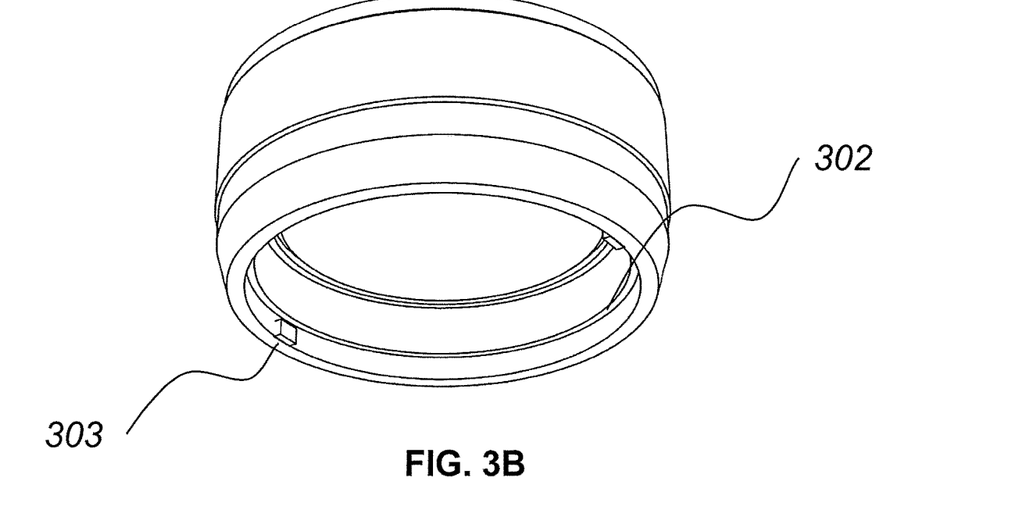
FIG. 3B is an enlarged bottom perspective view of the threaded smart pill cap shown in FIG. 3A.

FIGS. 3A and 3B illustrate alternative views of the smart pill cap 101 that is designed to fit with a "1-click" pill container. A thread 302 secures the smart pill cap to the pill container, with a rectangular block of plastic 303 that is incorporated into the smart pill cap 301 securing the 1-click mechanism that is built into the pill container. This ensures that the smart pill cap 301 remains securely fastened to the pill cap until the user presses the 1-click release mechanism on the container and twists the smart pill cap 301 to remove it.

Figure 4:
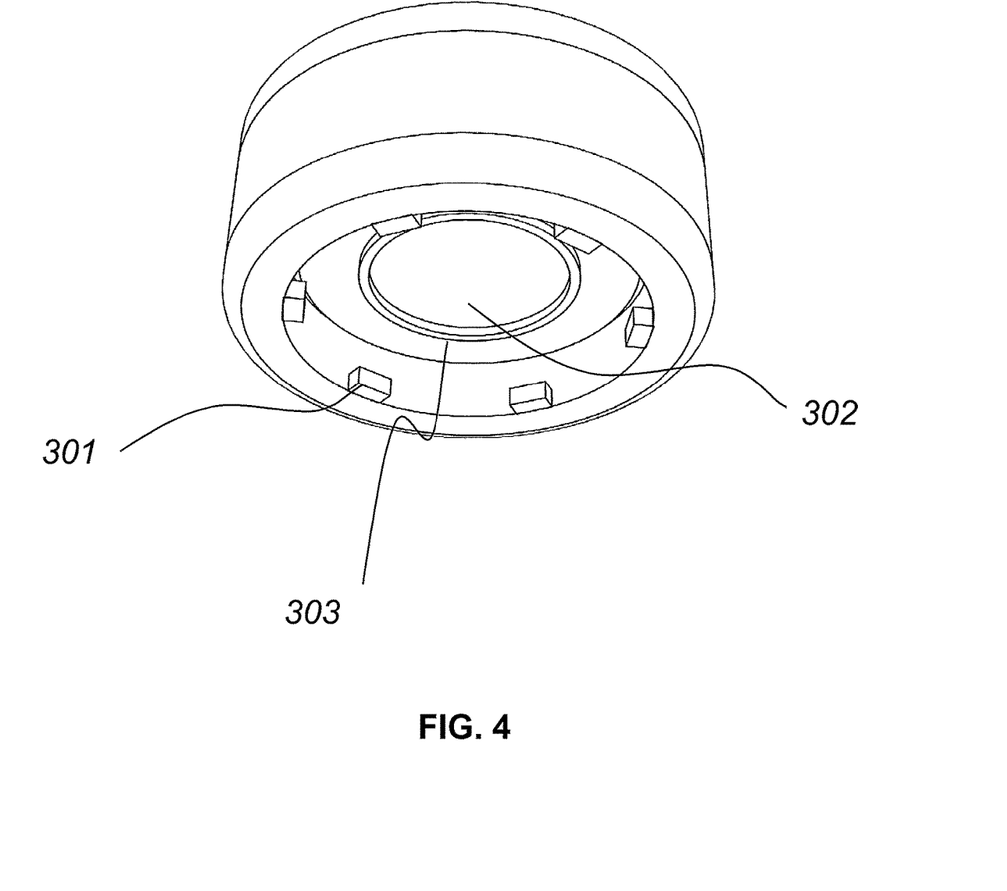
FIG. 4 is an enlarged bottom perspective view of a smart pill cap according to another embodiment of the disclosure, wherein the smart pill cap is childproof.

FIG. 4 illustrates a further alternative version of the smart pill cap 101 that is designed to integrate with a childproof pill container. In this embodiment, rectangular blocks of plastic 301 are integrated to the smart pill cap that fit with plastic "hooks" that are included on the external portion of a childproof pill container when the smart pill cap is pushed onto the childproof pill container. The sliding plate 302 selectively activates, for example, by pressing against, the switch type contact sensor when the container is attached to the smart pill cap. A ridge 303 is included on the sliding plate 302 in order to maintain a tight seal with the mouth of the pill container.

Figure 5:
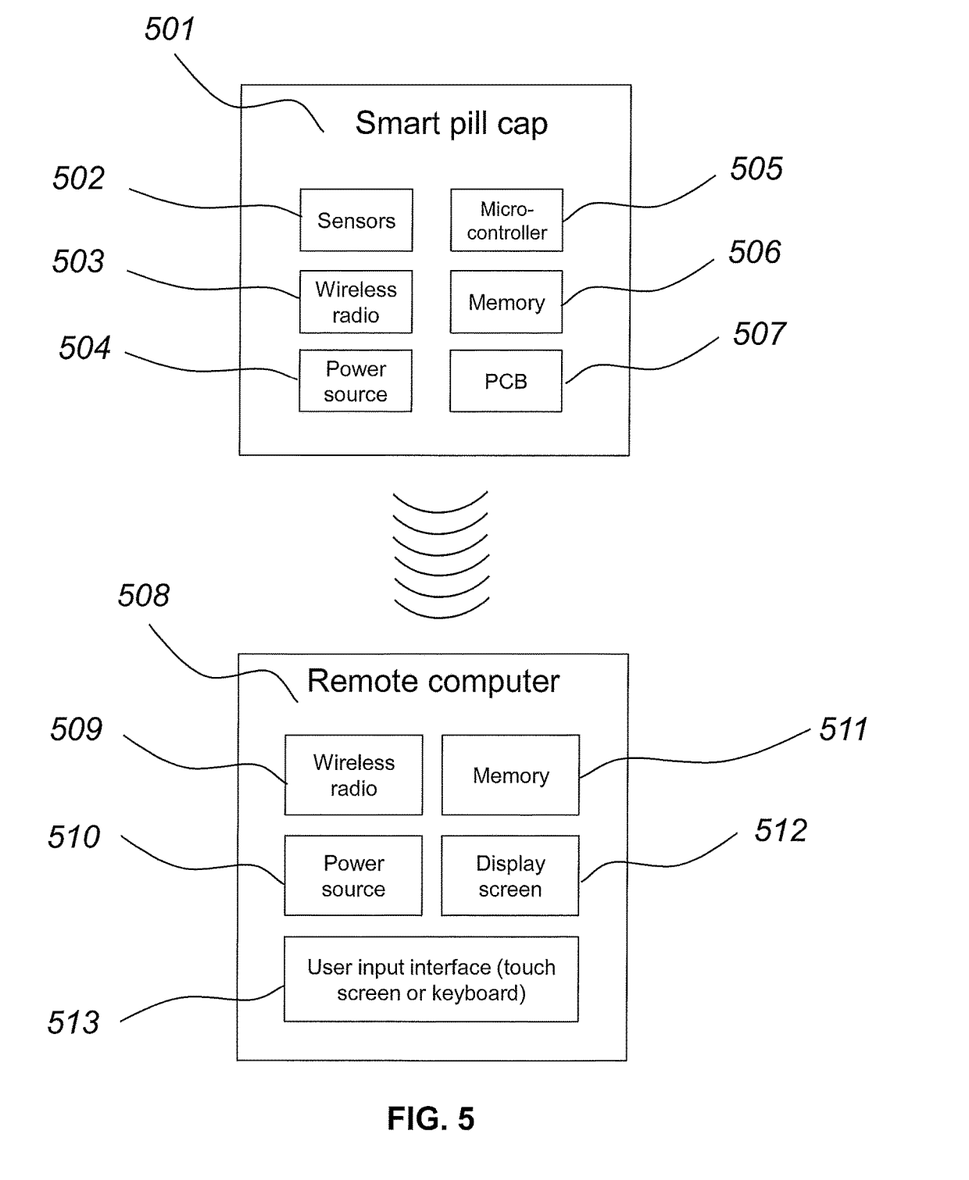
FIG. 5 is a schematic diagram illustrating an example communication relationship between the smart pill cap and pill container of FIG. 1 and a smartphone application.

FIG. 5 illustrates a medication adherence system comprising a smart pill cap 501, also described hereinabove and shown in FIGS. 1 and 2 as reference number 101, that transmits information that is sensed by the switch-based sensor 502 to a remote computer 508, such as a smartphone, tablet computer, or laptop computer, by transmitting information digitally from the smart pill cap's wireless radio 503 to the wireless radio contained in the remote computer 508. The smart pill cap stores data in local memory 506 that is transmitted whenever the smart pill cap 501 and remote computer 508 are connected and are in range. A power source 504 such as a lithium or lithium-ion battery is contained inside the smart pill cap and components are connected via a printed circuit board (PCB) 507.

The remote computer receives has the capability to store data from the smart pill cap in local memory 511. The remote computer also contains an onboard power 510 source, such as a lithium ion battery. Most importantly the remote computer serves as the user's primary means of viewing data that is collected by the smart pill cap, with the user of the smart pill cap having the ability to view said data on the display screen 512 of the remote computer 512 as well as to input data that can be sent from the remote computer 508 to the smart pill cap 501, such as a schedule of times when the user is supposed to take the medications contained by the smart pill cap 501 and the pill container that it is mated to.

Figure 6:
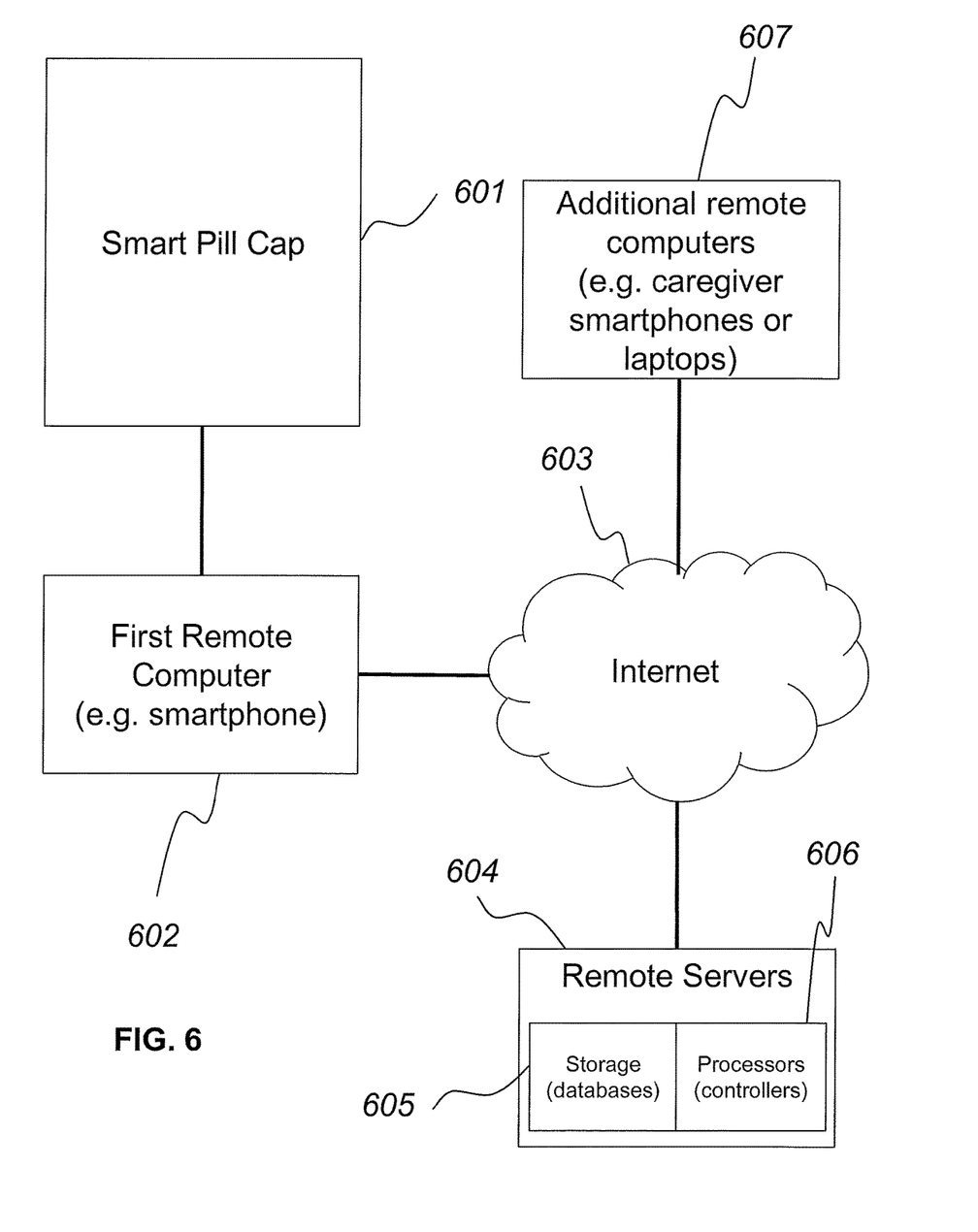
FIG. 6 is a schematic diagram illustrating an example of one network architecture between the smart pill cap, and remote servers that store the web application.

FIG. 6 illustrates a medication adherence network architecture comprising the system described in FIG. 5. The remote computer 602 sends information received from the smart pill cap 601, also described hereinabove and shown in FIGS. 1 and 2 as reference number 101, to a remote server 604 through the Internet 603. The remote servers having storage 605 and processing capabilities 606.

Data related to the user's medication adherence may be stored in the smart pill cap, the remote computer, and on the remote server, with data periodically synced across all three locations. Medication adherence data stored on the smart pill cap may be deleted after a specified number of events in order to free up additional memory, preferably after data is pushed to the remote computer or remote servers. Information may also be sent from the remote servers to the user's remote computer. For example, information may be sent to the user's smartphone related to pricing at various pharmacies where they can refill their medications.

Optionally, a portion of the data captured by the smart pill cap may be shared from the remote servers to additional remote computers 607 that are managed by remote caregivers, care managers, family members, or healthcare professionals (doctors, nurses, physician's assistants, etc.). This sharing is likely to be executed via an application programming interface (API) that is made available to users that have 1) received permission from the owner of the smart pill cap and first remote computer 2) have proven their credentials to the API through an authentication method, such as OAuth, a known open standard for authorization, or a token-based authentication method. This capability provides additional users to see information that can help them to care for the user, such as to intervene when the user has deviated from their medication schedule. Moreover, the API enables 3rd party solution providers to write custom software applications that combine data from the smart pill cap with data from other sources. For example, the additional remote computers may combine data from the smart pill cap with data from a wireless scale or a wireless blood pressure monitor to determine if the user has a high degree of risk of heart attack due to the user's deviation from their prescribed medication regimen.

Figure 7:
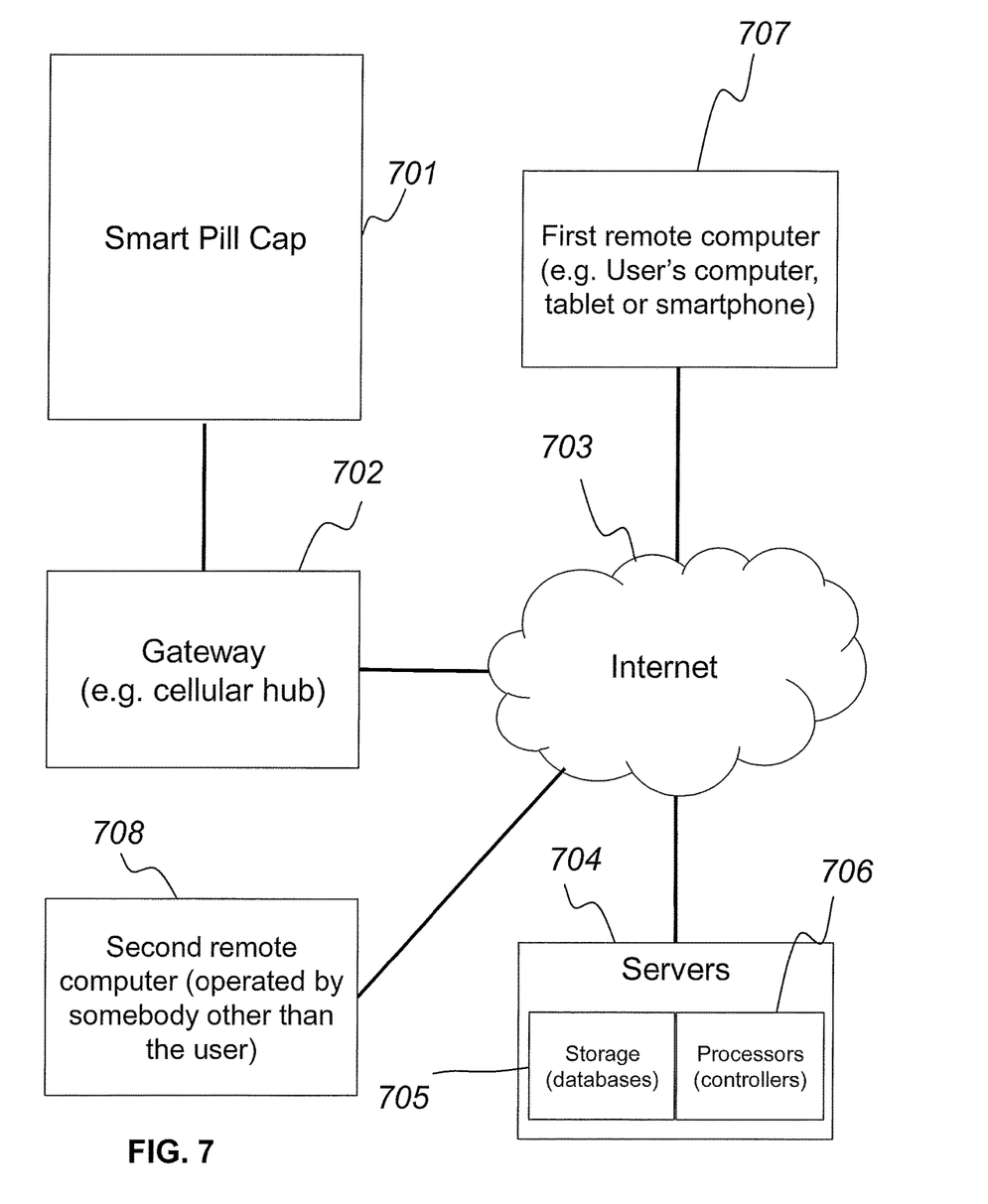
FIG. 7 is a schematic diagram illustrating an example network architecture where the smart pill cap sends a wireless signal to a cellular gateway, which relays medication adherence information to remote servers through the Internet, which then routes medication adherence data to devices used by the patient and members of their care team.

FIG. 7 illustrates a medication adherence system whereby the smart pill cap 701, also described hereinabove and shown in FIGS. 1 and 2 as reference number 101, sends data related to a user's medication adherence to a wireless hub 702 that is located within a close proximity (less than 2000 feet) that subsequently relays the data to remote servers 704. The remote servers are able to send the medication adherence data transmitted originally from the smart pill cap 701 to at least one of the user's smartphone 707 or to remote computers 708 being operated by the user's caregiver, family member or a healthcare professional. This represents a different network architecture that requires an additional intermediate gateway device 702 that is not required in the architecture described in FIG. 6. However this architecture does not require the user to own a smartphone or other device. In this case, the gateway 702 may also receive data sent by additional remote monitoring devices, such as wireless scales, blood pressure monitors, glucose monitors, motion sensors or other devices, most likely by using a wireless connection.

Figure 8:
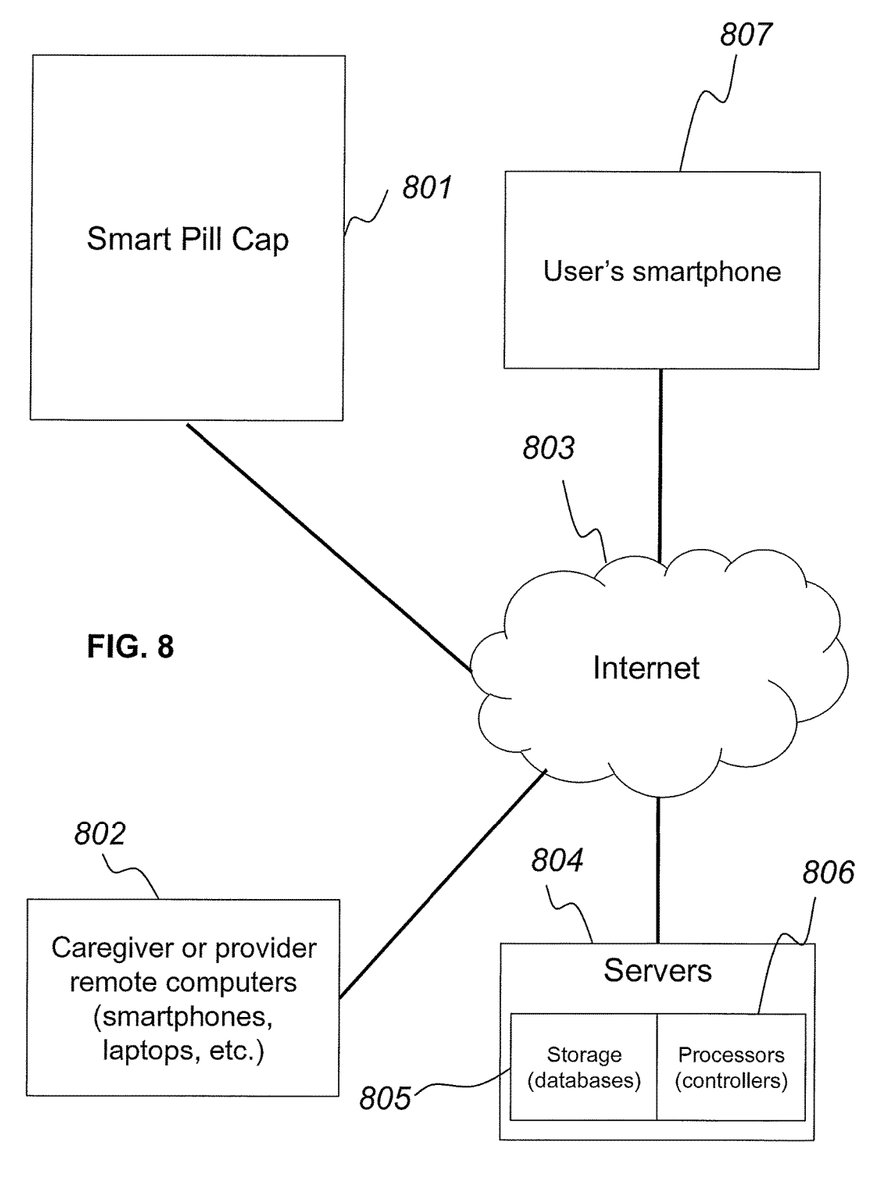
FIG. 8 is a schematic diagram illustrating an example network architecture according to another embodiment of the disclosure.

FIG. 8 illustrates a medication adherence network architecture whereby the smart pill cap 801, also described hereinabove and shown in FIGS. 1 and 2 as reference number 101, sends data directly to remote servers 804 through a cellular data connection without passing data through an intermediate hub or remote computer, such as those that were described in FIG. 6 and FIG. 7. In this case, the remote servers 804 may relay data collected by sensors in the smart pill cap 801 to the user's remote computer, or to remote computers operated by people other than the user. The cellular connection used in this architecture may be GSM, CDMA, LTE or another network type.

Figure 9:
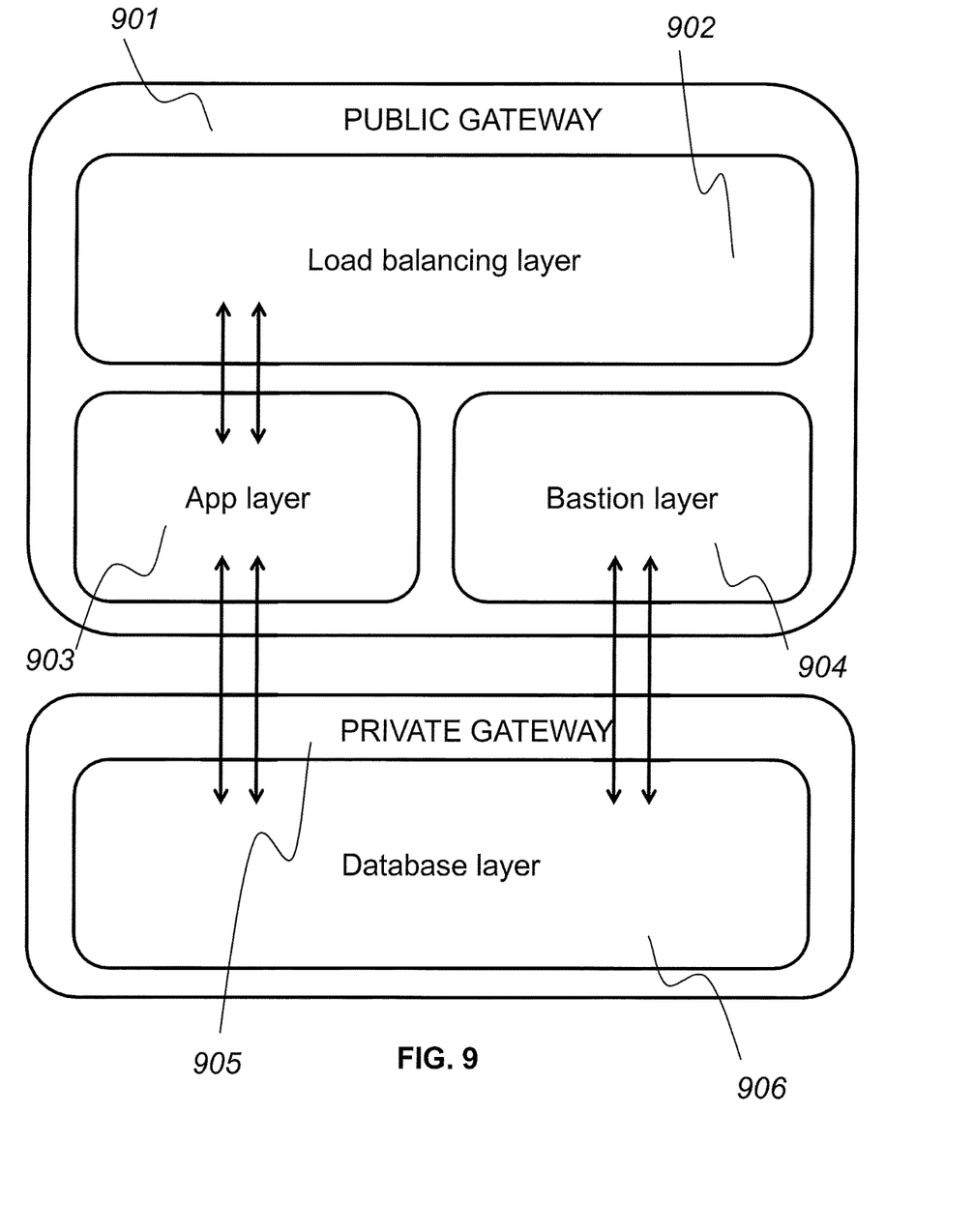
FIG. 9 is a particular embodiment of a data structure for preserving securing within the remote servers.

FIG. 9 illustrates an architecture for securely storing data collected by the smart pill cap described in FIG. 1 on a remote server. Requests to a first remote server come in through a public gateway 901, with requests being routed to a second remote server through the load balancing layer 902. This helps to ensure maximum responsiveness and uptime by distributing the computational load among a network of servers. Requests are routed to the app layer 903 of a web application or API that is designed specifically to be complimentary to the smart pill cap device described in FIG. 1. This app layer 903 can may requests to database layer 906 only through a private gateway 905. By limiting extraction of data from the database layer to a small subset of known servers, this helps to ensure security of the medication adherence data. All data stored in the server is also encrypted and servers are kept in locations that are physically secure. A bastion layer 904 running on one or more servers receives requests from protected areas of the network and is designated with specific responsibilities, such as security privileges and access privileges.

Figure 10:
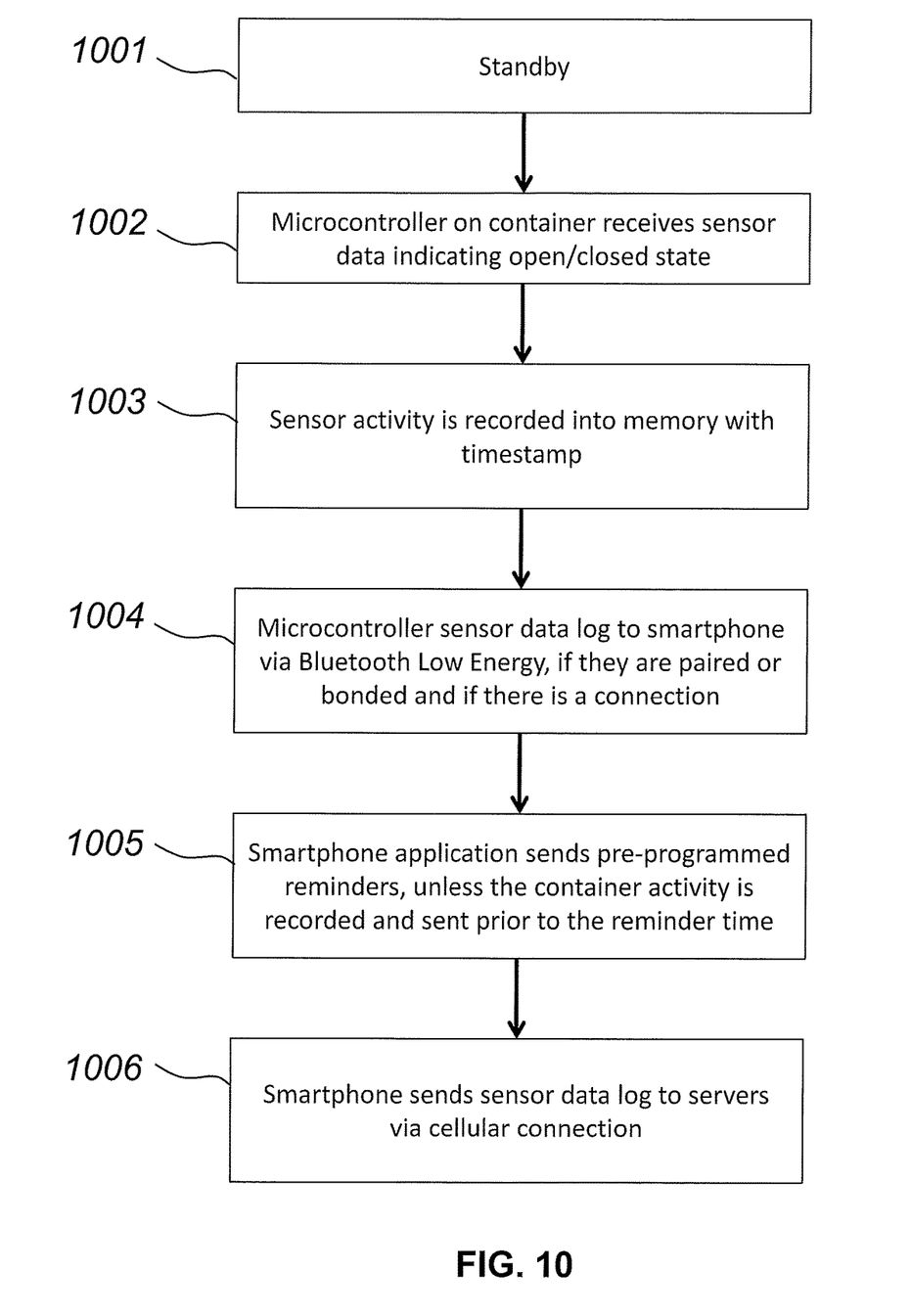
FIG. 10 is a flow diagram illustrating a method for sharing information from the smart pill cap to a remote server through an intermediary remote computer, according to one embodiment of the disclosure.

FIG. 10 illustrates a method for recording medication adherence data into memory located in a smart pill cap and sending that information to remote servers via a smartphone intermediary. The smart pill cap will remain in standby mode 1001 until it senses a change to opened/closed state, at which point it will enter "active mode" for a predefined period of time. Standby mode may be designed to conserve power by reducing the advertising interval frequency by the wireless radio. Once sensor data is detected 1002 it will be recorded into memory 1003 located on the smart pill cap. When the smart pill cap connects to a smartphone that it is paired to, it sends the data log to a complimentary application running on the smartphone 1004. The smartphone is pre-programmed to send medication reminders to the user unless it receives data from the smart pill container indicating that the smart pill container has been opened within a time interval designated to be associated with the scheduled medication event 1005. The smartphone also sends the sensor data log over the Internet using a cellular, WiFi, or other wireless connection 1006.

Figure 11:
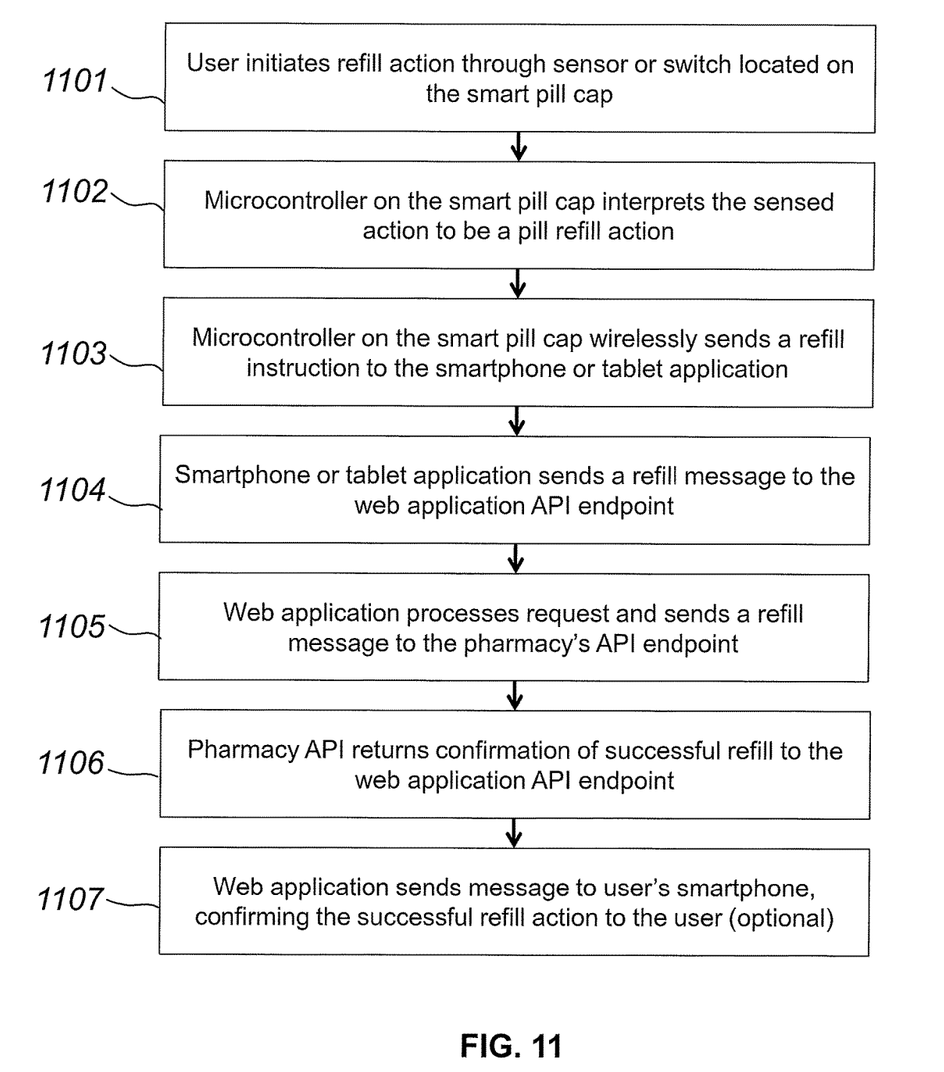
FIG. 11 is a flow diagram illustrating a method for initiating a prescription refill through the smart pill cap, according to another embodiment of the disclosure.

FIG. 11 illustrates a method for initiating a refill of a prescription medication, vitamin, or over-the-counter medication by interacting directly with the smart pill container. The user initiates the refill action by initiating the sensor located inside of the smart pill cap 1101 using a pre-defined action, such as pressing the sliding plate two or three times quickly, or by tapping the container on the table. The microcontroller within the smart pill cap interprets the sensed action to be a pill refill action 1102, and sends a pill refill request to the user's remote computer (e.g. smartphone) during the next session when the two devices communicate wireless 1103. The remote computer relays this refill message to a web application's API endpoint 1104, with the web application relating the refill request to a specific medication known to be taken by the user. The web application converts this into a refill request that can be send to a pharmacy's API endpoint 1105, including information the pharmacy can use to identify the specific prescription such as the Rx number, store ID, and possibly some information used to identify the individual (name, social security number, phone number, etc.). Optionally this request may be routed through one or more intermediate APIS, such as an ePrescription web service, prior to being routed to the pharmacy. At this point the pharmacy has received information instructing them to refill the prescription, which may help them comply with regulations requiring user-initiated actions to refill prescriptions. Optionally, the pharmacy API may return confirmation to the original web service that the prescription was successfully received 1106, with the web application relaying that message to the user's remote computer 1107 through a mobile application that is also capable of communicating with the smart pill container. The pharmacy's API may send additional messages to the user to provide updates on the status of the prescription refill, such as indication of when it is ready to be shipped or picked up.

Figure 12:
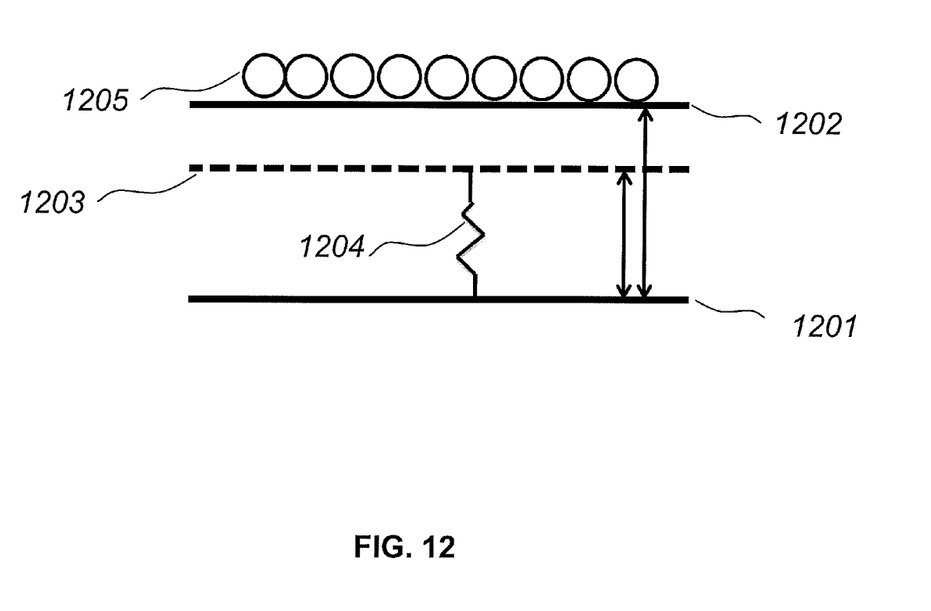
FIG. 12 is schematic illustration of a smart pill cap that is capable of sensing and calculating the weight of the contents of the attached pill vial.

FIG. 12 illustrates a method for integrating a method for detecting weight into the smart pill cap. In order to use this design, the smart cap and pill must be placed upside-down, with the contents of the pill container resting on the smart pill cap in an attached position. The weight of the pills presses on the sliding plate internal to the smart pill cap, for example, the sliding plate 204 described hereinabove. The sliding plate rests on a spring 1204; this spring can be the spring included in the sensor switch.

As shown in FIG. 12, a capacitor is created through two metallic plates, the first plate 1201 of which is attached to the printed circuit board. The second metallic plate is integrated into the sliding plate, and may consist of a sliding plate that is coated in a metallic material on the side of the plate that is not in contact with the contents of the pill container. The sliding plate may move between a first position 1202 when the contents of the container are empty, and a second position 1203 when the contents of the container are full and there is a greater force imposed on the plate. Capacitance is sensed by the printed circuit board and correlated to a measured distance, based on previous empirical experimentation. A weight is calculated based on Hooke's law, which holds that the displacement of a spring is proportional to the weight and the spring constant. The spring 1204 in the pushbutton may be used to provide the resistive force to the weight of the pills 1205 that are resting on the sliding plate 1201. Calibration is required to correlate weight to capacitance, which may be measured by creating a delay line consisting of the capacitive sensor and a large resistor (~10M Ohm).

In another embodiment, the pushbutton itself is used as a capacitive weight sensor.

In yet another embodiment, a load sensor is used that is attached to the printed circuit board.

In a further embodiment, scattered light is used to measure the distance between the PCB and the sliding plate. An infrared LED and complementary photoreceiver are placed in proximity on the side of the printed circuit board that is facing the sliding plate. Scattering from the sliding plate results in reflections of a portion of the illuminated light onto the photoreceiver, with the intensity of the light being proportional to the distance between the two plates. This illumination is best enabled in short bursts or on command in order to conserve energy.

From the foregoing description, one ordinarily skilled in the art can easily ascertain the essential characteristics of this disclosure and, without departing from the spirit and scope thereof, make various changes and modifications to the disclosure to adapt it to various usages and conditions.

What is claimed is:

1. An electronic sensing cap for a pill container, comprising:
   a housing with a top portion and a bottom portion and defining a cavity therebetween;
   a sliding plate disposed in the cavity adjacent to the bottom portion;
   a microcontroller with a switch type contact sensor disposed in the cavity between the top portion and the sliding plate, the sliding plate configured to slide upward and activate the contact sensor where the cap is secured to the pill container in a closed state, and the sliding plate configured to slide downward from and not activate the contact sensor where the cap is removed from the pill container in an open state;
   wherein the microcontroller further comprises a printed circuit board that comprises a non-infrared wireless radio, a memory, a speaker, and wherein a battery is connected to the printed circuit board that is powered at least in part in both the opened state and the closed state; and
   wherein the microcontroller is configured to non-infraredly, wirelessly transmit information indicative of an opening and a closing of the pill container over time to at least one of a smartphone or a tablet computer and/or a cellular gateway device.

2. The cap of claim 1, wherein the microcontroller is configured to store in the memory information corresponding with the sliding plate pressing up against the switch type contact sensor, the information indicative of an opening and a closing of the medication container over time.

3. The cap of claim 1, wherein the microcontroller is configured to cause the speaker to emit an audio reminder according to a predetermined schedule.

4. The cap of claim 1, wherein the bottom portion of the housing has internal threads configured to cooperate with external threads of the container, and at least one rectangular block of plastic beneath the internal threads, configured to securely fasten the pill cap to the container until the user presses down on the cap in a one-click action and twists the cap to remove it from the container.

5. The cap of claim 1, wherein the top portion of the housing has a removable top plate that permits access to the cavity and the battery upon removal.

6. The cap of claim 1, further comprising a band disposed on an outer perimeter of the cap, flush to a cap side, covering a seam between the top portion and the bottom portion, and colored to associate with a specific pill.

7. The cap of claim 6, wherein the top portion is a top piece and the bottom portion is a bottom piece, the top piece formed separately from the bottom piece, the top piece affixed to the bottom piece to form the housing, and at least one of the top piece and the bottom piece defines a groove on an outer surface thereof, the groove extending around an entirety of the cap, the band disposed in the groove.

8. The cap of claim 1, wherein the microcontroller further includes a sensor configured to measure a weight of contents of the container where the container is turned upside down.

9. The electronic sensing cap of claim 1, wherein a cap data is able to be wirelessly synced from one of the cellular-enabled remote computers and/or the cellular gateway device through an internet to a remote server, and the remote server is configured to receive the data through an application program interface (API), store an encrypted data in the memory, and process the encrypted data on a central web application, the API first checking for an authorization and a credential prior to granting access; and wherein the data is synced from a central web application to a second web application that is run by a healthcare provider and/or by a secure web-based API.

10. The electronic sensing cap of claim 1, wherein the microprocessor within the cap, is programmed to remain in a first low energy standby mode until the switch type contact sensor is activated, upon which the microprocessor enters a second high energy active mode for a predefined period of time.

11. The electronic sensing cap of claim 1, wherein the microprocessor within the cap is programmed to schedule transmission of a wireless data on a regularly scheduled basis regardless of the contact sensor input, and varies one of a transmission power, or a reduced wireless radio advertising interval frequency, in response to a data that is received by the contact sensor.

12. A system for promoting adherence to a regimen by a patient, comprising:
a cap for a pill container, including a housing with a top portion and a bottom portion and defining a cavity therebetween, a sliding plate disposed in the cavity adjacent to the bottom portion, and a microcontroller with a switch type contact sensor disposed in the cavity between the top portion and the sliding plate, the sliding plate configured to slide upward and activate the contact sensor where the cap is secured to the pill container in a closed state, and the sliding plate configured to slide downward and not activate the contact sensor where the cap is removed from the pill container in an open state; wherein the microcontroller further comprises a printed circuit board that comprises a non-infrared wireless radio, a memory, a speaker, and a battery connected to the printed circuit board that is powered at least in part in both the opened state and the closed state; and
a first remote computer having a memory and a display, the first remote computer in non-infrared wireless electronic communication with the cap and configured to show on the display information corresponding with the sliding plate activating the switch type contact sensor, the information indicative of an opening and a closing of the pill container over time.

13. The system of claim 12, wherein the first remote computer is one of a personal computer, a tablet, and a smartphone of the patient.

14. The system of claim 13, wherein the smartphone or tablet is pre-programmed to send pill reminders to the patient, unless the smartphone or tablet non-infrared wirelessly receives data from the pill container indicating that the pill container has been opened within a time interval designated to be associated with a scheduled pill event.

15. The system of claim 12, further comprising a cellular gateway in non-infrared wireless communication with both the cap and the first remote computer.

16. The system of claim 12, further comprising a second remote computer in non-infrared wireless communication with the first remote computer over the Internet.

17. The system of claim 16, wherein the second remote computer provides access to the information to one of a caregiver and a provider of the patient.

18. A method for promoting adherence to a regimen by a patient, the method comprising the steps of:
providing a system including a cap for a pill container, the cap having a housing with a top portion and a bottom portion and defining a cavity therebetween, a sliding plate disposed in the cavity adjacent the bottom portion, and a microcontroller with a switch type contact sensor disposed in the cavity between the top portion and the sliding plate, the sliding plate configured to slide upward and activate the contact sensor where the cap is secured to the pill container in a closed state, and the sliding plate configured to slide downward and not activate the contact sensor where the cap is removed from the pill container in an open state,
wherein the microcontroller further comprises a printed circuit board that comprises a non-infrared wireless radio, a memory, a speaker, and a battery connected to the printed circuit board that is powered at least in part in both the opened state and the closed state; and
a first remote computer having a memory and a display, the first remote computer in non-infrared wireless electronic communication with the cap and configured to show on a display information corresponding with the sliding plate activating the contact sensor, the information indicative of an opening and a closing of the pill container over time, wherein the first remote computer is a smartphone or a tablet computer;
maintaining the cap in a standby mode until the cap senses a change in state from one of the open state and the closed state;
causing the cap to enter an active mode, the cap configured to record the information from the contact sensor in the active mode;
creating by the microcontroller of the cap a sensor data log of the information; and
communicating non-infrared wirelessly from the microcontroller of the cap to the first remote computer the sensor data log.

19. The method of claim 18, further comprising the step of sending non-infrared wirelessly pill reminders to the patient by the first remote computer unless the first remote computer receives information from the cap indicating that the container has been in the open state within a time interval designated to be associated with a scheduled pill event.

20. The method of claim 18, further comprising the steps of,
initiating a refill action by a pre-defined action on the cap by a user, the predefined action comprising, pressing the sliding plate two or three times quickly, or by tapping the pill container on the table, the microcontroller detecting the predefined action and causing the microcontroller to non-infrared wirelessly send a refill request to the first remote computer;
relaying the refill request wirelessly by the first remote computer to a second remote computer through an API endpoint with a web application;
relaying the refill request wirelessly by the web application to a pharmacy computer running a pharmacy application, wherein the refill request comprises information to identify the prescription and patient;
relaying a confirmation message from the pharmacy application to the web application API endpoint; and
the web application processing a successful refill confirmation and wirelessly sending a message to the first remote computer confirming a successful refill action by the pharmacy computer.

21. A method for ordering a refill of a vitamin or a medication in a pill container, comprising:
providing a system with a wireless network connecting a cap for a pill container, a first remote computer, a second remote computer with a refill request web application installed thereon, and a remote pharmacy computer, the cap including a housing with a top portion and a bottom portion and defining a cavity therebetween, a sliding plate disposed in the cavity adjacent to the bottom portion, and a microcontroller with a switch type contact sensor disposed in the cavity between the top portion and the sliding plate, the sliding plate configured to slide upward and activate the contact sensor;

wherein and the microcontroller further comprises a printed circuit board that comprises a non-infrared wireless radio, a memory, a speaker, and a battery connected to the printed circuit board that is powered at least part in both the opened stated and the closed state;

a first remote computer comprising a user's personal computer, a tablet, or a smartphone, having a memory and a display, and in non-infrared wireless electronic communication with the cap and configured to show on the display information corresponding to a refill request;

initiating a refill action by a pre-defined action on the cap by the user, the predefined action comprising pressing the sliding plate two or three times quickly, or by tapping the pill container on the table, and causing the microcontroller to non-infrared wirelessly send a refill request to the first remote computer;

relaying the refill request wirelessly by the first remote computer to a second remote computer with a refill request web application installed thereon, wherein the web application refill request comprises information to identify the prescription and a patient, comprising at least one of, a prescription number, a store identification, and/or a patient identification information;

relaying the refill request wirelessly by the second remote computer web application to a pharmacy computer, wherein the refill request comprises the information to identify the prescription and the patient;

transmitting a confirmation of a refill completion wirelessly by the pharmacy computer to the second remote computer web application; and transmitting the confirmation of the refill completion wirelessly by the second remote computer web application to the first remote computer.

* * * * *